(12) United States Patent
Szabados et al.

(10) Patent No.: US 7,915,007 B2
(45) Date of Patent: Mar. 29, 2011

(54) FIXATIVE FOR FIXING BIOLOGICAL MATERIALS

(75) Inventors: Andreas Szabados, Grünwald (DE);
Roberto Gerigk, Mühldorf a. Inn (DE)

(73) Assignee: Biosepar-Gesellschaft fur Medizin-und Labortechnik mbH, Grunwald (DE)

( * ) Notice: Subject to any disclaimer, the term of this patent is extended or adjusted under 35 U.S.C. 154(b) by 778 days.

(21) Appl. No.: 11/676,414

(22) Filed: Feb. 19, 2007

(65) Prior Publication Data

US 2008/0057536 A1    Mar. 6, 2008

(30) Foreign Application Priority Data

Aug. 29, 2006    (DE) .......................... 10 2006 040 315

(51) Int. Cl.
*G01N 1/30* (2006.01)
*G01N 33/48* (2006.01)

(52) U.S. Cl. ...................................................... 435/40.5

(58) Field of Classification Search .................. 435/40.5
See application file for complete search history.

(56) References Cited

U.S. PATENT DOCUMENTS

| | | | |
|---|---|---|---|
| 4,100,158 | A | 7/1978 | Hydes et al. |
| 4,148,870 | A | 4/1979 | Hydes et al. |
| 5,260,204 | A | 11/1993 | Heckl et al. |
| 5,422,277 | A | 6/1995 | Connelly et al. |
| 6,531,317 | B2 | 3/2003 | Guirguis et al. |
| 2001/0031482 | A1 | 10/2001 | James et al. |
| 2005/0074422 | A1 | 4/2005 | Visinoni |
| 2005/0084924 | A1 | 4/2005 | Shults et al. |

FOREIGN PATENT DOCUMENTS

| | | |
|---|---|---|
| DE | 3822183 A1 | 2/1990 |
| DE | 3824936 A1 | 3/1990 |
| DE | 4404544 A1 | 8/1995 |
| GB | 1440283 | 6/1976 |
| JP | 402169779 A * | 6/1990 |
| WO | 03029783 A1 | 4/2003 |

OTHER PUBLICATIONS

Abstract of DE 3822183; Feb. 8, 1990.
Abstract of DE 3824936; Mar. 22, 1990.
Abstract of DE 4404544; Aug. 17, 1995.
"Hexamethylentetramin" [Online] Feb. 2005, Georg Thiemeverlag, XP002464945, <www.roempp.com/prod/roempp.php>.
"Amin-Formaldehyd-Additions- und -Kondensationsprodukte" [Online] Dec. 2007, Georg Thieme-Verlag, XP002464946, <www.roempp.com/prod/roempp.php>.

* cited by examiner

*Primary Examiner* — Ruth A Davis
(74) *Attorney, Agent, or Firm* — Senniger Powers LLP

(57) ABSTRACT

A fixative for fixing biological materials contains a depot agent, preferably a polyamine and especially hexamethylenetetramine, which reacts chemically with positively charged ions, especially H+ from an acid, while forming a fixative, where the fixative is an aldehyde and especially formaldehyde, which in turn reacts chemically with the biological material to be fixed in order to fix it and is consumed in doing so. By adjusting the pH of a solution containing the depot agent, a chemical equilibrium reaction occurs between the depot agent, fixative and biological material, so that just as much fixative is continuously formed as can be immediately consumed by the biological material. With that, the fixative, and especially the hazardous formaldehyde, cannot escape. Thus, an externally formaldehyde-free fixative that at the same time has the excellent fixative properties of formaldehyde is created.

9 Claims, No Drawings

FIXATIVE FOR FIXING BIOLOGICAL MATERIALS

CROSS-REFERENCE TO RELATED APPLICATION

This application claims priority from German Patent Application No. 10 2006 040 315.0 filed on Aug. 29, 2006, the entire disclosure of which is expressly incorporated by reference.

DESCRIPTION

The invention concerns a fixative for fixing biological materials, such as tissues, cells, organs and secretions from humans and animals, also bacteria, viruses, fungi and parasites, as well as biotechnological products, etc.

Formaldehyde (formalin), which has excellent fixative properties even over a long period of time, is chiefly used as fixative today. Aldehydes, and especially formaldehyde, however, are considered to be highly toxic. Formaldehyde was categorized as a substance with a valid suspicion of having cancer-causing potential and it can cause allergies and irritation of skin, the respiratory tract and the eyes. At high dosage it can even be acutely life threatening. It also has a pungent unpleasant odor. Also, the use of formalin is legally limited for reasons of environmental protection.

There are already a number of approaches for creating a formalin-free fixative, as described in DE 38 22 183 A1 for example, in which tannic acid is proposed as an important component of a fixative. DE 38 24 936 A1 proposes, for rapid fixing, a hot water treatment with an adjuvant of tannic acid and an additional adjuvant containing a dihydric alcohol and water.

DE 44 04 544 A1 does away with chemical fixatives like formalin entirely by denaturing with physical heat in water baths. This type of fixing, however, involves the disadvantage that the morphological structures of the material to be fixed can be altered. For example, proteins can coagulate. This is why this method cannot be used for all materials.

Generally a fixative should keep organic materials like tissues, cells, cell clusters, viruses, bacteria, parasites, fungi, stool, etc., in a stable state for as long as possible after taking a sample. The condition of the sample therefore should be fixed so that in later examinations, for example, under a microscope, the condition at sampling is still present. Thus, the morphological structure of the sample should be preserved. Bacteria, fungi and viruses must not propagate and no other kind of unwanted chemical or physical processes should take place. In summary, a fixative should keep all materials of biological origin in a stable condition for analytical and preparative purposes.

The approaches in the prior art described above aim at completely avoiding the use of formalin by replacing the formalin by nontoxic or less dangerous substances that, however, should otherwise as far as possible have the same good fixative properties as formalin.

The task of this invention is to create a fixative of the kind mentioned above that has the good properties of formalin, but does not bring with itself the hazards of formalin or other aldehydes.

This task is solved by the characteristics given in Claim 1. Advantageous embodiments and developments of the invention can be taken from the dependent claims.

The basic idea of the invention is to specify an aldehyde-free and especially formaldehyde-free depot agent that in a chemical reaction forms a fixative, which in turn can be consumed by the organic substance in order to fix it. The fixative that results from the said chemical reaction can contain aldehydes and especially formaldehyde. The chemical reaction is initiated by positively charged ions, which are preferably made available through an acid environment. The resulting amounts of aldehydes and especially formaldehyde are so low that danger to the user or the environment can be avoided.

Thus, a chemical equilibrium reaction takes place. The fixative that results from the depot agent in very small amounts due to the reaction with the acid will in turn enter into a chemical reaction with the organic substance and in doing so be completely consumed, so that no fixative can escape.

The basis is the following chemical equilibrium reaction:

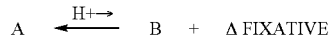

where Δ means a very small amount.

A is a starting substance, namely the said depot agent; B is a second substance that arises in the reaction and can be the fixative noted above, i.e., an aldehyde-like formaldehyde.

The above reaction goes in both directions, so that an equilibrium reaction takes place. If a sample of organic or biological material is present at this equilibrium reaction it consumes the fixative that is present in small amounts, which disrupts the equilibrium state and leads to the formation of new fixative, which is illustrated by the following equation:

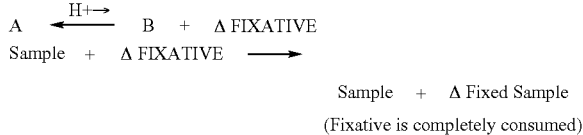

This reaction continues until all of the sample is fixed.

A system that optimally satisfies this condition works with a polyamine in accordance with the following system:

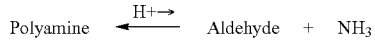

NH$_3$ and condensation products with NH$_3$, namely polyamines, are toxically safe in lower concentrations and in certain concentrations are even permitted in the food industry.

The said equilibrium reaction can be adjusted via the pH value. Up to a pH of about 7.0 polyamines are stable. At a pH less than 7.0 the equilibrium begins to shift in the direction of aldehyde+NH$_3$. Advantageously, therefore, the pH is adjusted so that just the minimal amounts of aldehyde are formed. The pH region for this is in the range of pH 1.0-7.0, preferably 3.5-7.0, and still more preferably 3.5-4.0. If the pH value is close to the neutral value of 7.0, very little aldehyde is formed, while if it closer to 1.0, relatively much more aldehyde forms. The adjustment of the pH, however, in practice is also dependent on the amount of the biological material to be fixed. In the case of larger amounts to be fixed larger amounts of aldehydes are also necessary, so that then the pH value is adjusted to acid solutions.

Instead of polyamines, related substances are also possibilities, for example, hexamethylenetetramine, triazines (for example, 1,3,5-tris(2-hydroxyethyl)-1,3,5-hexahydrotriazine, 1,3,5-triazine-1,3,5(2H,4H,6H)-triethanol) and imidazoles (for example, 1,3,4,6-tetrakishydroxymethyltetrahydroimidazo(4,5)imidazole-2,5-dione, tetramethylolacetylenediurea), which likewise have properties that make them suitable for fixatives. The latter chemicals are also suitable as fixatives in the basic region in solution. A reason for this lies in the fact that as soon as processes that involve exchange of electrons begin in the sample, for example, oxidation, metabolization by microorganisms, decomposition processes, charges for releasing aldehydes become available. These processes are stopped by local fixing. It is assumed that the pH values are not so high that the sample is destroyed, for example by hydrolysis. For this reason the user should operate in a weakly acid to basic environment. Then buffered solutions of the polyamines and related substances with pH values between 4.5 and 11 can likewise also be suitable as fixatives in accordance with the invention.

The fixative in accordance with the invention can be made available in a solution. However, it is also possible to make it available in dry form, for example, as a powder, a tablet or as a coating on a container, and only activated upon use by adding a solvent like water. Transport costs, among other things, can be reduced by this.

A specific embodiment example uses a solution containing 1 wt % hexamethylenetetramine as depot agent and other substances like an additional acid that serves to adjust the pH. Organic or inorganic acids such as citric acid can, as desired, be used here. Ascorbic acid, which primarily serves as antioxidant, can be used as another additive. In addition, ethylene glycol, which serves as a mediator for the lipid phases of the sample and also as a moisturizer can also be used. Instead, sorbitol, glycerol, propylene glycol and similar substances can, as desired, also be used. A surfactant as a wetting aid can be added as an additional additive, for example, Triton 200 or other nonionic surfactants. Finally, fragrances can also be added, for example, terpenes with aldehyde function, for example, geraniol or citral, and these substances also act as biocides.

EXAMPLE

A solution of the following chemicals, in percent by weight, was formed, and its pH was adjusted to 3.0-4.0:

| | |
|---|---|
| 1% | hexamethylenetetramine |
| 1% | citric acid |
| 1% | ascorbic acid |
| 2% | ethylene glycol |
| 0.05% | surfactant |
| 0.01% | geraniol |
| 0.01% | citral |
| Remainder | water to 100% |

This solution was tested on stool samples and flawlessly preserved them for 30 days. 3.5 mL solution was used for the stool test. Solutions containing hexamethylenetetramine in a concentration up to 1% do not have to be labeled as hazardous substances. The dose of hexamethylenetetramine that is dangerous for an adult is 4 g. The amount of hexamethylenetetramine in the 3.5 mL of solution thus is extremely far below the hazardous concentration. The solution is neither combustible nor highly corrosive nor caustic. Absorption through the skin or respiratory tract is excluded. Thus, all in all, an improvement of working and transport safety is ensured.

The amounts indicated above can be modified in each case according to application. For example, the value of 1 wt % hexamethylenetetramine is preferred, since at this amount there is no legal labeling requirement as a hazardous substance. For many application purposes, in which larger amounts of fixative are required, this value can however also be increased considerably, and then the solution will require labeling.

Also, the said value of 1 wt % citric acid, which is primarily responsible for adjusting the pH, can be matched to requirements in order to shift the described equilibrium reaction in the reaction of the formation of more formaldehyde.

The other indicated values can easily be varied by the specialist in each case according to the desired properties. One should note here that water is not the only possibility for the rest of the formulation; other aqueous solutions or other suitable solvents such as alcohols are also possibilities.

The following substances are also possibilities as depot agents:

Protectol HT, from BASF containing
  CAS Number: 4719-04-4
  EINEC Number: 225-208-0
  Molecular Formula: $C_9H_{21}N_3O_3$
  Molecular Weight: 219
  Chemical Name: 1,3,5-tris-(2-hydroxyethyl)-1,3,5-hexahydrotriazine, 1,3,5-triazine-1,3,5(2H,4H,6H)-triethanol Protectol TD, from BASF containing
  CAS Number: 5395-50-6
  EINEC Number: 226-408-0
  Molecular Formula: 262
  Chemical Name: 1,3,4,6-tetrakishydroxymethyltetrahydro-imidazo(4,5)imidazole-2,5-dione, tetramethylolacetylenediurea The following substances can also be used as depot agents: glutaraldehyde, glyoxal, chloralhydrate, propanal, butanal, ethanal, which each form complexes with $NH_3$.

The invention claimed is:

1. A method of fixing a biological material, the method comprising:
   reacting hexamethylenetetramine and an acid in a composition adjusted to a pH between 3.0 and 7.0 to produce a biological material fixative, wherein the biological material fixative further comprises:
   1-15% by weight hexamethylenetetramine;
   1-15% by weight citric acid;
   1-15% by weight ascorbic acid;
   2-15% by weight ethylene glycol;
   0.05-5% by weight surfactant;
   0.01-1% by weight geraniol; and
   0.01-1% by weight citral; and
   contacting the biological material with the fixative to facilitate consumption of the fixative by the biological material in equilibrium with the fixative, thereby maintaining the biological material in stable condition for analytical or preparative purposes.

2. The method of claim 1 wherein the fixative is free of formaldehyde.

3. The method of claim 1 wherein the fixative is free of aldehyde.

4. The method of claim 1 wherein said pH is between 3.5 and 4.0.

5. The method of claim 1 wherein the biological material fixative comprises:
   1% by weight hexamethylenetetramine;
   1% by weight citric acid;
   1% by weight ascorbic acid;
   2% by weight ethylene glycol;
   0.05% by weight surfactants;

0.01% by weight geraniol; and
0.01% by weight citral.

6. The method of claim 1 wherein the biological material fixative is made into powder form, tablet form, or a coating on a container which is activated by adding a solvent at the time of said contacting.

7. A method of fixing a biological material, the method comprising:
reacting hexamethylenetetramine and an acid in a composition adjusted to a pH between 1.0 and 7.0 to produce a biological material fixative, wherein the biological material fixative further comprises:
1-15% by weight hexamethylenetetramine;
1-15% by weight citric acid;
1-15% by weight ascorbic acid;
2-15% by weight ethylene glycol;
0.05-5% by weight surfactant;
0.01-1% by weight geraniol; and
0.01-1% by weight citral; and
contacting the biological material with the fixative to facilitate consumption of the fixative by the biological material in equilibrium with the fixative, thereby maintaining the biological material in stable condition for analytical or preparative purposes.

8. The method of claim 7 wherein said pH is between 2.0 and 7.0.

9. A method of fixing a biological material, the method comprising:
reacting hexamethylenetetramine and an acid in a composition adjusted to a pH between 1.0 and 7.0 to produce a biological material fixative, wherein the biological material fixative further comprises:
1-15% by weight hexamethylenetetramine;
1-15% by weight citric acid;
1-15% by weight ascorbic acid;
2-15% by weight of a moisturizer selected from the group consisting of sorbitol, glycerol, propylene glycol, and combinations thereof;
0.05-5% by weight surfactant;
0.01-1% by weight geraniol; and
0.01-1% by weight citral; and
contacting the biological material with the fixative to facilitate consumption of the fixative by the biological material in equilibrium with the fixative, thereby maintaining the biological material in stable condition for analytical or preparative purposes.

\* \* \* \* \*